United States Patent [19]

Huber-Emden et al.

[11] 4,055,599
[45] Oct. 25, 1977

[54] N-(ALKYLHYDROBENZYL)-ALKYLTHIO- AND MERCAPTO-ACETAMIDES

[75] Inventors: Helmut Huber-Emden; Karl Eschle, both of Basel; Arthur Maeder, Therwil, all of Switzerland

[73] Assignee: Ciba-Geigy Corporation, Ardsley, N.Y.

[21] Appl. No.: 611,043

[22] Filed: Sept. 8, 1975

Related U.S. Application Data

[63] Continuation-in-part of Ser. No. 69,886, Sept. 4, 1970, Pat. No. 3,927,091, which is a continuation-in-part of Ser. No. 737,832, June 18, 1968, abandoned.

[30] Foreign Application Priority Data

June 23, 1967 Switzerland ................. 8947/67

[51] Int. Cl.$^2$ ................................. C07C 103/38
[52] U.S. Cl. .................................... 260/562 S
[58] Field of Search ........................ 260/562 S

[56] References Cited

U.S. PATENT DOCUMENTS

| 3,590,083 | 6/1971 | Dexter et al. | 260/562 S |
| 3,780,103 | 12/1973 | Knell | 260/562 S X |

FOREIGN PATENT DOCUMENTS 1,207,461 10/1970 United Kingdom ............ 260/562 S

*Primary Examiner*—Allen B. Curtis
*Assistant Examiner*—Thomas A. Waltz
*Attorney, Agent, or Firm*—Nestor W. Shust

[57] ABSTRACT

The present invention provides carboxylic acid amides of the formula

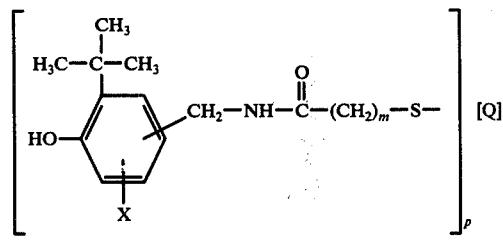

in which X represents methyl or tertiary butyl, $m$ is the integer 1 or 2, Q represents hydrogen, alkyl, alkylidene, cycloalkylidene, substituted methylene, alkylene, alkenylene or a 3,4,5 or 6-valent saturated aliphatic hydrocarbon radical and $p$ represents an integer which corresponds to the valency of the radical Q. These carboxylic acid amides are suitable for stabilizing organic materials sensitive to oxidations.

6 Claims, No Drawings

N-(ALKYLHYDROBENZYL)-ALKYLTHIO- AND MERCAPTO-ACETAMIDES

This is a continuation-in-part of our application Ser. No. 69,886, filed Sept. 4, 1970, now U.S. Pat. No. 3,927,091 which in turn is a continuation-in-part of our patent application Ser. No. 737,832, filed June 18, 1968, now abandoned.

The present invention provides the new carboxylic acid amides of the formula

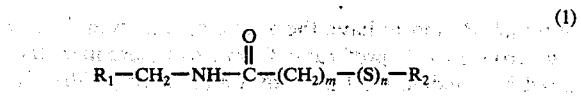
(1)

in which $R_1$ represents a benzene residue which contains a hydroxyl group in ortho- or para-position to the —$CH_2$— group and as further substituents two hydrocarbon residues, $R_2$ represents a hydrogen atom a possibly substituted alkyl radical containing 1 to 20, preferably 1 to 18 carbon atoms, a possibly substituted aryl radical, a residue of the formula

in which $R_1$ and $m$ have the above meanings, or a residue of the formula

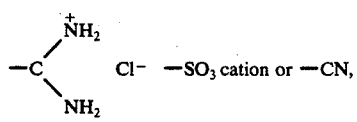

in which $m = 1$ or 2 and $n$ is a digit not greater than 7.

Such carboxylic acid amides are accessible by known methods. Thus the carboxylic acid amide of the formula (2)

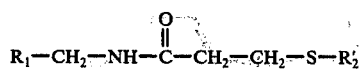

$R_1$ has the above meaning and $R_2'$ represents an alkyl radical which may be substituted or a residue of the formula (2a)

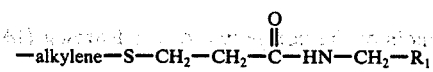

are formed by the reaction in the presence of an alkaline catalyst of a compound of the formula (3)

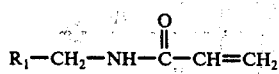

with a monomercaptoalkyl compound in the molar ratio 1:1 or with a dimercaptoalkyl compound in the molar ratio 2:1.

The compounds needed as starting materials for this additive reaction can be manufactured from dialkylhydroxybenzenes and acrylylmethylolamide by the so-called Tscherniak condensation. Then it is possible to add mercapto compounds, for example simple alkylmercaptans such as n-propylmercaptan or n-dodecylmercaptan on to the double bond of the resulting condensation products of the formula (2). The alkyl groups of these mercaptans may also contain substituents, for example such as can be further reacted, such as carboxylic acid alkyl ester groups. If the compounds of the formula (3) are to be reacted with alkane-dithiols, this is advantageously performed at a molecular ratio of 2:1, and the two mercapto groups add on to a double bond each of the two molecules of the acrylic acid derivative. Alkaline catalysts suitable for the additive reaction are, for example, sodium ethylate or benzyl trimethyl ammonium hydroxide.

Compounds of the formula

(4)

(in which $R_1$, $m$ and $n$ have the above meanings) are obtained when a compound of the formula

(5)

(in which $R_1$ and m likewise have the above meanings) are reacted at a molecular ratio of 2:1 with a sodium sulphide of the formula $Na_2S_n$ where n is a digit not exceeding 7, for example 1, 2 or 5. The halogen compounds of the formula (5) are obtained, as described for the compounds of the formula (3), by Tscherniak condensation of dialkylhydroxybenzenes with halogenalkanecarboxylic acid methylolamides containing 1 or 2 carbon atoms in the alkane residue, for example chloropropionylmethylolamide or preferably chloroacetylmethylolamide. The condensation of the halogen compounds of the formula (5) with the sodium sulphides is advantageously conducted in a neutral organic solvent; sodium sulphides that contain more than one sulphur atom for every two sodium atoms, can be manufactured in such solvents, for example in methanol, immediately before the condensation and without intermediate isolation, from $Na_2S$ and elemental sulphur.

Compounds of the formula (4), in which $m = 2$, are obtained when $H_2S$ is added on, in the presence of a minimal quantity of NaHS, to compounds of the formula (3), for example

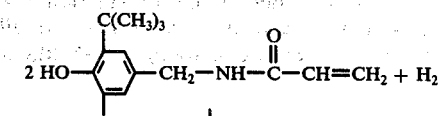
(6)

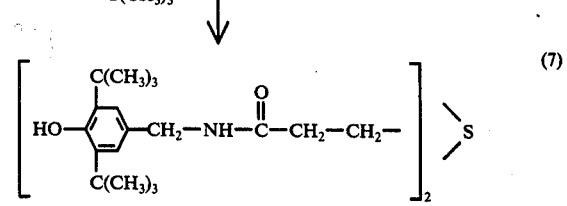
(7)

Compounds of the formula

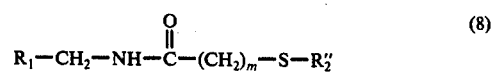
(8)

in which $R_1$ and m have the above meanings and $R_2''$ is a possibly substituted alkyl radical, an aryl radical or a residue of the formula

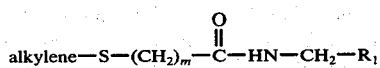 (9)

wherein the alkylene group contains 1 to 10, preferably 1 to 8 carbon atoms, are obtained when compounds of the formula

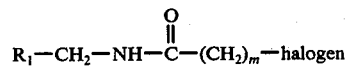 (10)

are condensed with mercapto compounds of the formula $H-S-R_2'''$, in which $R_2''$ represents a possibly substituted alkyl or aryl radical, or when compounds of the formula (10) are condensed with dimercapto compounds of the formula H—S-alkylene—S—H at a molecular ratio of 2:1. When a halogen compound containing a —$CH_2$—$CH_2$— group (m = 2) is used, some of the resulting compounds correspond to those of the formula (2) obtained by adding acrylic acid derivatives of the formula (3) on to mono or di-mercaptoalkyl compounds. When $R_2''$ in the compound of the formula $H-S-R_2''$ is a substituted alkyl radical, suitable substituents are again, for example, carboxylic acid alkyl esters. As suitable aryl radicals there may be specially mentioned benzene residues containing as substituents, for example, alkyl groups such as ethyl or methyl, alkoxy groups such as ethoxy or methoxy, or halogen atoms, especially chlorine.

Carboxylic acid amides of the formula

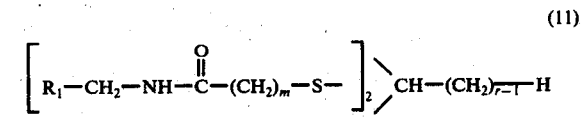 (11)

in which $R_1$ and m have the above meanings and r is a digit from 1 to 20, preferably from 1 to 18, are manufactured by condensing 2 mols of a mercaptan of the formula

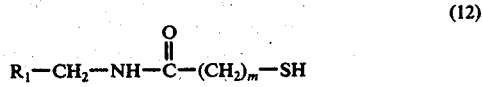 (12)

with 1 mol of an aldehyde of the formula $$O=CH-(CH_2)_{r-1}H. \quad (13)$$

Compounds of the general formula (8) are obtained, for example, when intermediates of the formula (5) are condensed in stoichiometric amounts with other polyfunctional mercapto compounds, for example (a)

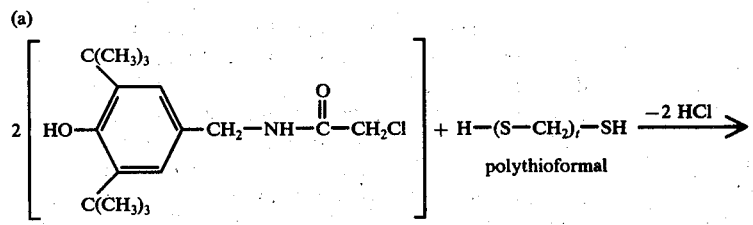

t = 2 to 5 on an average

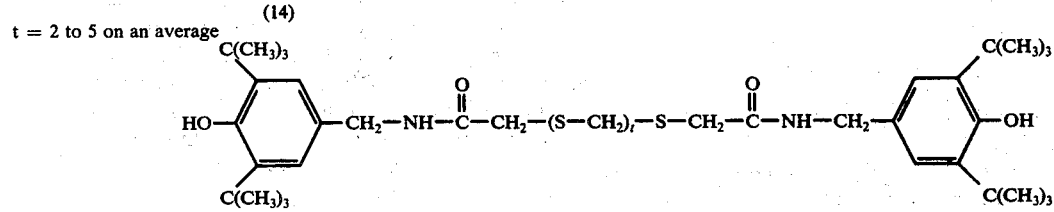

b. 4 mols of the compound of the formula (14)

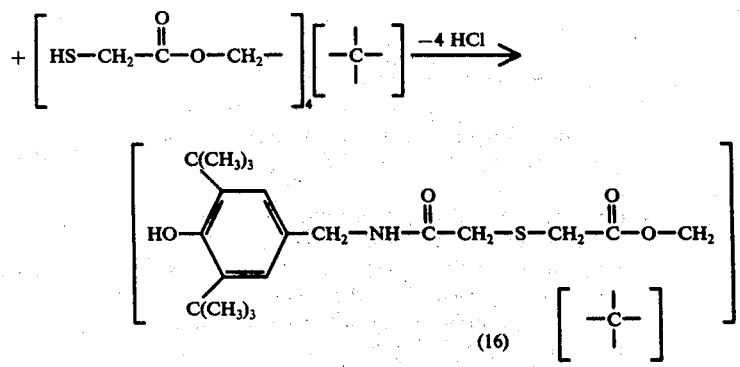

Compounds of the general formula (8) ($m = 1$; $R_2'' =$ substituted alkyl radical) are also obtained when mercaptans of the general formula

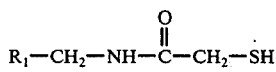 (17)

in which $R_1$ has the above meaning are added on to formaldehyde at a molecular ratio of 1:1, for example:

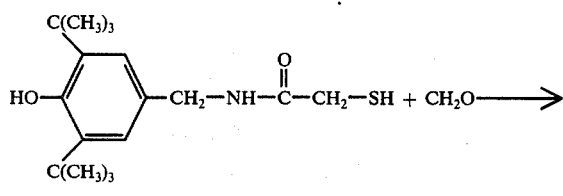

(18)

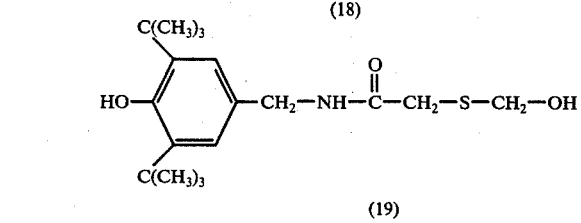

(19)

Compounds of the general formula (8) ($m = 1$, $R_2'' =$ substituted alkyl radical) are also obtained, for example, when mercaptans of the general formula (12) are condensed with aldehydes or ketones at a molecular ratio of 2:1, for example: 2 Mols of the compound of the formula (18)

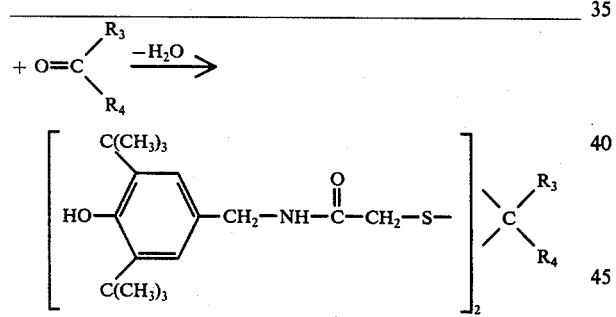

where

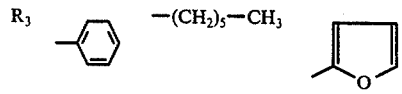

| R$_4$ | —H | —H | —H | |
|---|---|---|---|---|
| N° | (21) | (22) | (23) | (24) |

The preferred compounds correspond to the formula

 (25)

in which $R_1$ and $m$ have the above meanings, $s = 1$ or 2, $p$ is a digit from 1 to 6, B represents a p-valent, possibly substituted alkyl radical which may contain vinyl groups, and A represents a residue of the formula —CH$_2$—COO—CH$_2$—, are obtained by condensing p mols of a mercaptan of the formula

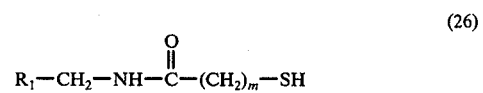 (26)

in form of its alkali metal salt with 1 mol of a p-functional alkylhalide of the formula YZ$_p$ (27)

Compounds of the general formula (8) ($m = 1$; $R_2'' =$ substituted alkyl radical) are also obtained when mercaptans of the formula (17) in form of their alkali metal salts are condensed in stoichiometric proportions with suitable, possibly polyfunctional alkylhalides for example:

 (28)

$$YZ_p \xrightarrow{-p \cdot NaZ}$$

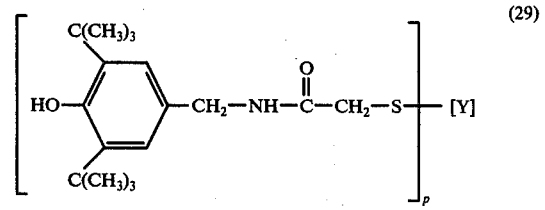 (29)

Z represents a chlorine or bromine atom and $p = 1$ to 6. In the compounds of the formula (29) thus obtained the symbols Y and $p$ have, for example, the following meanings:

| Formula No. | Y | p |
|---|---|---|
| 30 | —CH$_2$—C(Cl)=CH$_2$ | 1 |
| 31 | —CH$_2$— | 2 |
| 32 | —(CH$_2$)$_4$— | 2 |
| 33 | —(CH$_2$)$_8$— | 2 |
| 34 | —CH$_2$—CH=CH—CH$_2$— | 2 |
| 35 | $-\overset{\mid}{\underset{\mid}{C}}-H$ | . |
| 36 | $-H_2C-\overset{\overset{\mid}{CH_2}}{\underset{\underset{\mid}{CH_2}}{C}}-CH_2-$ | 4 |
| 37 | $-\overset{\mid}{\underset{\mid}{C}}-\overset{\mid}{\underset{\mid}{C}}-$ | 6 |

Thus, carboxylic acid amides manufactured from polyfunctional alkylhalides, preferably correspond to the formula

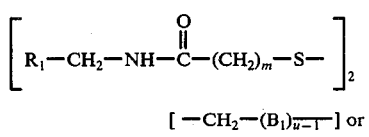  (38)

[ —CH$_2$—(B$_1$)$_{\overline{u-1}}$—] or

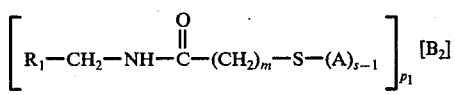  (39)

in which R$_1$ and $m$ have the above meanings, B$_1$ represents a residue of the formula —(CH$_2$—)$_v$— [in which v is a digit from 1 to 7] or of the formula —CH=λ CH—CH$_2$—, B$_2$ represents a residue of the formula

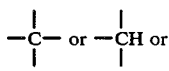

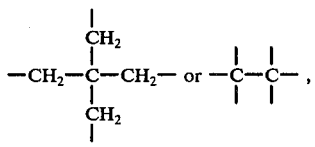

A stands for a residue of the formula —CH$_2$—COO—CH$_2$—, and $m$ and $s$ each is 1 or 2, and $p_1$ is 3, 4 or 6.

The compounds of the formula (1) obtained by the manufacturing methods described above may be converted into other compounds, some of them likewise corresponding to this formula, when they contain suitable reactive groups. Thus, carboxylic acid amides of the formula

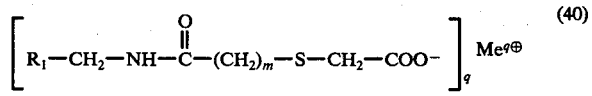  (40)

(in which R$_1$ and $m$ have the above meanings, Me is a q-valent cation and $q$ = 1, 2 or 3) are obtained when esters of the formula (41)

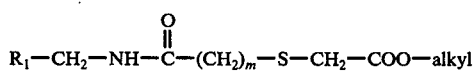

are hydrolyzed in an alkaline medium and, if desired, the resulting carboxylic acid salts are converted into the free acids or into other salts. The hydrolysis is easy to achieve with a solution of sodium hydroxide in ethanol or methanol. When the sodium salt is acidified in an aqueous medium, the free acid is obtained. When these acids are subjected to a double reaction with alkaline earth metal salts or heavy metal salts, for example with the water-soluble salts of barium, cadmium, zinc, tin, lead, copper, nickel or chromium or with uranyl salts, the corresponding salts of the acids of the formula (40) are obtained. Such salts are in general sparingly soluble in water, but as a rule soluble in organic solvents such as benzene or methylenechloride.

Carboxylic acid amides of the formula

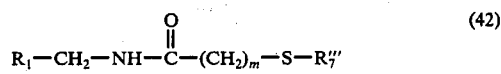  (42)

(in which R$_1$ and m have the above meanings and R''' represents an atomic grouping of the formula

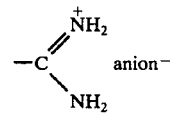

or a hydrogen atom) are obtained when compounds of the formula (5) are reacted with thiourea and, if desired, the resulting thiuronium salt is split, for example with aqueous sodium hydroxide.

Furthermore, the compounds of the formula (5) may be reacted with alkalithiocyanates accompanied by elimination of alkali metal halide, to yield compounds of the formula

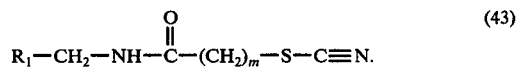  (43)

The residue R$_1$ in carboxylic acid amides of the formula (1) is a benzene residue which contains a hydroxyl group in ortho- or preferably in para-position to the —CH$_2$— group and as further substituents two hydrocarbon residues. As mentioned above, the residue R$_1$ is introduced into the intermediates used for the manufacture of the carboxylic acid amides by means of a corresponding hydroxybenzene that contains no substituent in at least one of the positions mentioned, being for example a 1-hydroxy-2,4-, 3,4-, -2,3-, -2,5- or -3,5-dialkylbenzene. These hydroxydialkylbenzenes contain in addition to any desired hydrocarbon residue, for example an ethyl or a methyl group, advantageously as at least one further substituent an alkyl group with a carbon atom which hinders sterically and is bound direct with the benzene nucleus, such as a tertiary butyl, tertiary octyl or tertiary dodecyl group, or a cyclohexyl residue, such as an unsubstituted cyclohexyl or the 1'-methylcyclohexyl residue, or an α-phenylalkyl residue, for example the benzyl residue.

Preferred carboxylic acid amides of the formula (11) contain a residue R$_1$ of the formula

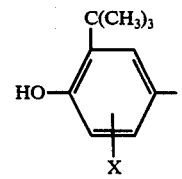

in which X represents a methyl or tertiary butyl group.

A preferred class of carboxylic acid amides of the invention has the formula

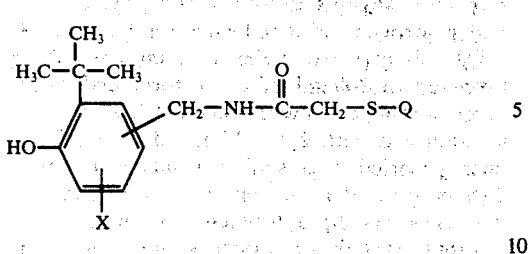

in which X is methyl or tertiary butyl and Q is alkyl containing 1 to 20 carbon atoms.

Another preferred class of carboxylic acid amides of the invention has the formula

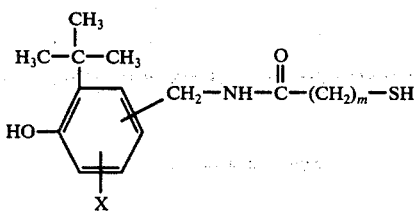

in which X is methyl or tertiary butyl, and m is the integer 1 or 2.

In a preferred subclass of the carboxylic acid amides described in the two immediately preceding paragraphs, X is tertiary butyl and is located in ortho-position to the hydroxyl and the amido-methylene residue is located in para-position to the hydroxyl.

The compounds of the formula (1) are suitable for stabilizing organic materials sensitive to oxidation. For this purpose they may be used in known manner for the following substrates:

Homopolymers are copolymers of ethylenically unsaturated compounds such as vinylchloride, vinylidenechloride, styrene, butadiene, isoprene, ethylene, propylene, derivatives of acrylic and methacrylic acid, for example acrylic acid alkyl esters, acrylic acid amides and acrylonitrile, for example, acrylonitrile-butadiene-styrene copolymers (ABS); polyamides, for example of E-caprolactam or of adipic acid and a diamine; polyesters such as polyterephthalic acid glycol esters; natural and synthetic rubbers; lubricating oils, gasoline, vegetable and animal oils and fats; waxes; cellulose and cellulose derivatives such as cellulose esters.

In general, a small quantity (0.01 to 2%, referred to the weight of the substance to be protected) of the compounds of the formula (1) suffices to achieve good protection from oxidation. The antioxidant may be incorporated with the material to be protected, for example, direct, that is to say by itself, or in combination with other additives such as plasticizers, pigments, light filters, optical brighteners, and/or with the aid of solvents.

The antioxidative effect of the compounds of the formula (1) is evident also in the exposure test since these compounds can prevent or strongly reduce any oxidative process caused by exposure to light, for example the yellowing of polyvinylchloride.

The symbols used in the formulae of the present description, such as $R_1$, $R_2$, m, n, have throughout the identical meaning which has been accurately defined at least once. Unless otherwise indicated, parts and percentages in the following Manufacturing Instructions and Examples are by weight.

Manufacturing Instructions for Starting Products

A. The starting material of the formula

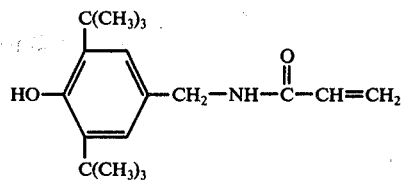

may be prepared in the following manner:

While cooling it to at most 20° C, a solution of 82.4 g of 1-hydroxy-2,6-di-tertiary butylbenzene in 470 ml of glacial acetic acid is mixed first with 135 ml of pyrophosphoric acid and then continuously within one hour with 40.4 g of acrylylmethylolamide. The batch is stirred until all has dissolved and kept for 2 days at room temperature in a stoppered flask, during which 10 g of a by-product [2,2', 6,6'-tetra-tertiary butyl-4,4'-methylene-biphenol]precipitate. This precipitate is suctioned off and the filtrate stirred into 2 liters of water. The tough precipitate formed is thoroughly stirred with fresh water, whereupon it crystallizes right through. The material is triturated and washed with water until it is free from acid. Yield: about 109 g of the compound of the formula (6), corresponding to 94% of theory. Melting point: 112° to 113° C, after recrystallization from cyclohexane.

In an analogous manner the starting materials of the following formulae are obtained:

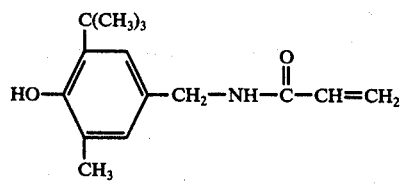

melting at 157° – 159° C

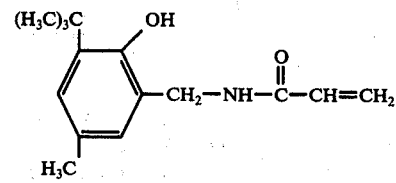

melting at 155° – 156° C

B. The compound of the formula

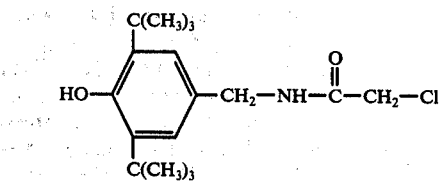

may be prepared in the following manner:

a. While cooling a solution of 82.4 g of 2,6di-tertiary butylphenol in 480 ml of glacial acetic acid at 20° C, 120 ml of pyrophosphoric acid and then continuously within 1 hour 54.4 g of chloroacetylmethylolamide are added. The batch is stirred overnight and then kept for 1 day in a stoppered flask, whereupon part of the reaction product cyrstallizes out; it is stirred into 2 liters of water, and the precipitate is washed free from acid, whereupon it yields about 115 g (= 92% of theory) of the compound of the formula (14) melting at 152° - 153° C after recrystallization from cyclohexane.

In identical manner the compounds of the following formulae are obtained:

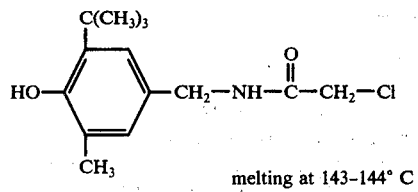
melting at 143-144° C (47)

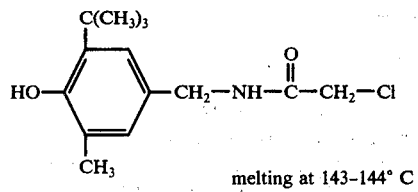
tough resin (48)

(CH₃)₃C, OH
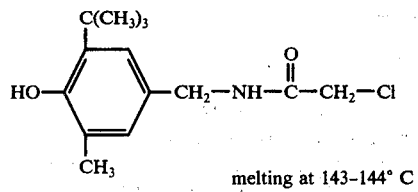
melting at 135-137° C (49)

(CH₃)₃C, OH
CH₂—NH—C(=O)—CH₂Cl [non-crystalline mixture of positional isomers]
OCH₃

Another method for the manufacture of the compound of the formula (14) is the following:

b. A solution of 257.5 g of 2,6-di-tertiary butylphenol in 375 ml of 100% acetic acid is mixed with 170 g of chloroacetylmethylolamide and while stirring it, hydrochloric gas is introduced until thick fogs appear at the CaCl₂-closure tube (duration 45 minutes). The reaction is exothermic. The temperature is maintained at 30° to 35° C by supplying external cooling. During this operation the chloroacetylmethylolamide dissolves. The batch is stirred on for 5 hours, whereupon the thick product settles out; it is suctioned off, washed acid-free with water and dried. The product can be purified by washing with ½ liter of cyclohexane. Yield: 80% of the theoretical of the compound of the formula (14).

EXAMPLE 1

A solution of 12 g of the compound of the formula (6) and 3.46 g of n-propylmercaptan in 70 ml of absolute ethanol is mixed with a freshly prepared solution of 0.1 g of sodium in 5 ml of absolute ethanol, whereupon the mixture heats up slightly by itself. It is kept for ½ hour under nitrogen and then heated for ¼ hour at 60° C, the solvent is expelled under vacuum, the oil residue is taken up in 200 ml of chloroform and extracted by successive agitation with 100 ml of N-sodium hydroxide solution and with 2 × 150 ml of water. The organic phase is dried over sodium sulphate and the solvent distilled off under vacuum. The residual thick oil crystallizes slowly through when kept for several months. Rapid crystallization occurs when the oil is seeded and thoroughly stirred for some time with 200 ml of petroleum ether. After filtering and drying there are obtained about 10.5 g (= 69.5% of theory) of the compound of the formula

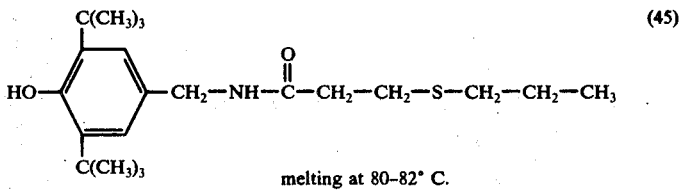
melting at 80-82° C. (45)

By using octanthiol-1 instead of n-propylmercaptan, the compound of the formula

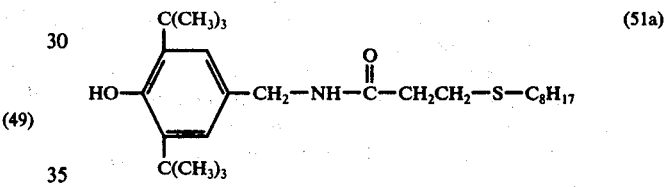
(51a)

melting at 48° to 49° C, is obtained.

In an identical manner the corresponding compounds that contain the residue —(CH₂)₁₁—CH₃ or —CH₂—OC—O—CH₃ instead of the n-propyl residue, and also the compound of the formula

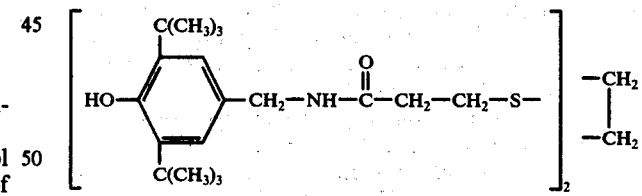
(52)

melting at 158° - 160° C.

In an identical manner ethanedithiol and the intermediates of the formula (45) or (46) respectively furnish the substances

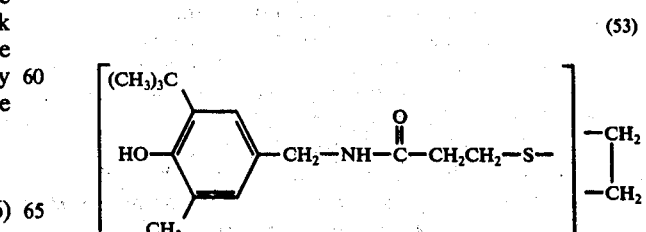
(53)

melting at 159° - 161° C about 13.2 g (= 100% of theory) of the compound of the formula

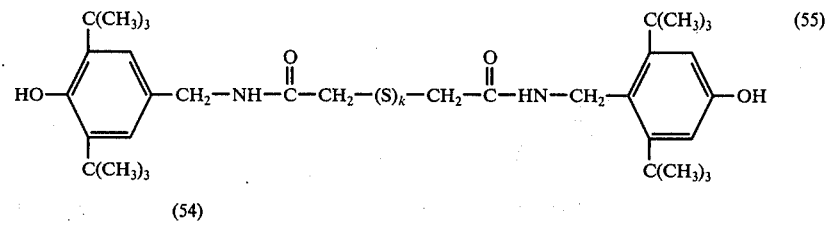

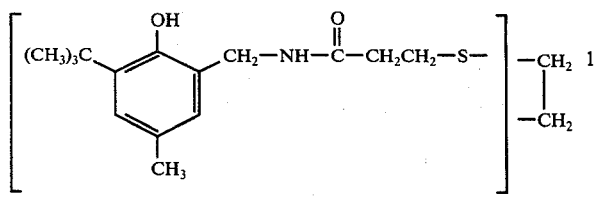

in which $k = 1$. After recrystallization from carbon tetrachloride it melts at 186° – 187° C.

By a similar reaction chloroacetic acid-(3-tertiary butyl-4-hydroxy-5-methylphenyl)-methylamide of the formula (47) furnishes the compound of the formula

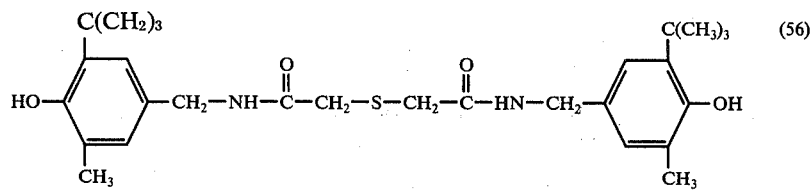

melting at 186° – 187° C.

melting at 147° – 149.5° C.

EXAMPLE 2

A solution of 14.5 g of the compound of the formula (6) in 100 ml of absolute ethanol saturated with $H_2S$ is mixed with a solution of 0.1 g of sodium in 10 ml of absolute ethanol and $H_2S$ gas is slowly passed through the solution for 6 hours. The solvent is then expelled under vacuum. The oily residue is taken up in 250 ml of benzene and agitated with 25 ml of 2N-NaOH, the benzolic phase is washed neutral with water, treated with sodium sulphate and active carbon and the solvent is expelled under vacuum, to yield 13.5 g (= 88% of theory) of the compound of the formula

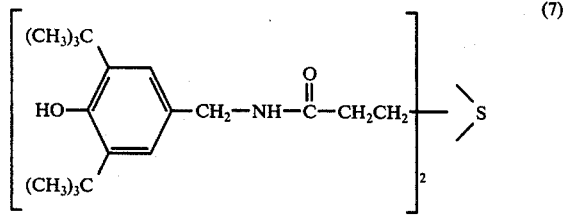

melting at 155° – 157° after recrystallization from carbon tetrachloride and then from benzene.

EXAMPLE 3

A solution of 2.88 g of crystalline sodium sulphide of 61% strength in 100 ml of methanol is mixed with 14 g of the compound of the formula (14) which dissolves rapidly and a slightly exothermic reaction sets in. After ½ hour the batch is heated for ½ hour at 50° C, then cooled, the precipitated sodium chloride is suctioned off and the solvent expelled under vacuum. The crystalline residue is thoroughly washed with water and yields

EXAMPLE 4

A solution of 2.88 g of crystalline sodium sulphide of 61% strength in 100 ml of methanol is mixed with 2.88 g of sulphur; the batch is refluxed for 10 minutes, then cooled again to room temperature and mixed with 14 g of the compound of the formula (14) which dissolves while the solution is heating up, and a short time later a precipitate begins to form. The whole is refluxed for ½ hour, allowed to cool, suctioned and the filter residue is thoroughly washed with water, to yield about 10.8 g (= 67.4% of theory) of the compound of the formula (55) in which $k = 5$. After recrystallization from ethanol this product decomposes at about 100° C.

When a correspondingly smaller quantity of sulphur is dissolved in the methanolic sodium sulphide solution, all other conditions being identical, the compound of the formula (55) with $k = 2$ is obtained; it melts at 178° – 180° C.

EXAMPLE 5

A solution of 4.96 g of thiophenol in 45 ml of molar absolute ethanolic sodium ethylate solution is mixed under nitrogen with a solution of 14 g of the compound of the formula (14) in 150 ml of absolute ethanol. A slightly exothermic reaction sets in immediately and sodium chloride settles out. The batch is refluxed for 15 minutes and the precipitated sodium chloride is suctioned off. (Yield: 2.6 g = 100% of theory). The filtrate is freed from the solvent under vacuum, the crystalline residue dissolved in 200 ml of chloroform and thoroughly agitated with 100 ml of 2N-sodium hydroxide solution and with 2 × 100 ml of water. The extracts are dried with sodium sulphate and the chloroform is expelled under vacuum, to yield a crystalline residue of about 17.3 g (= 100% of theory) of the compound of the formula

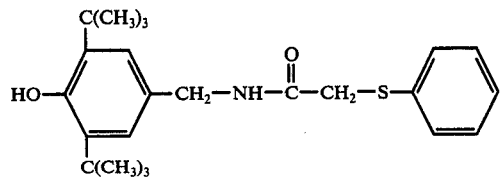

which after recrystallization from cyclohexane melts at 115° – 116° C.

When the corresponding mercaptans (or ethanedithic) and chloroacetic acid amides (see Manufacturing Instructions B) are used, under otherwise identical conditions, the compound of the formula

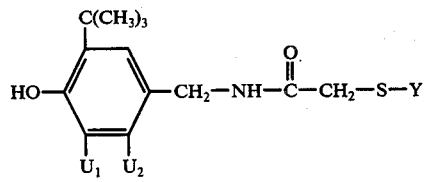

(58)

is obtained according to the following Table I.

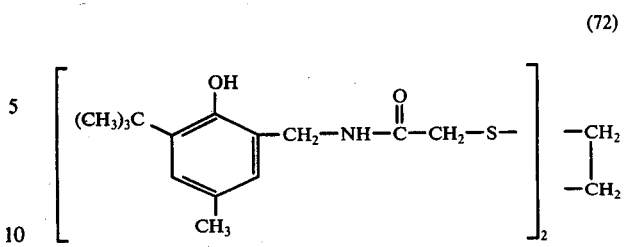

(72)

melting at 162° – 164° C.

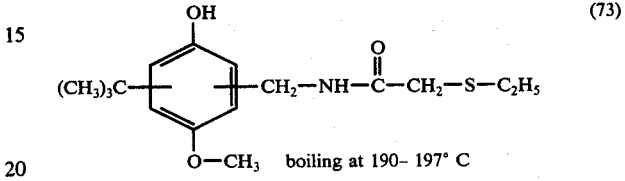

(73)

boiling at 190– 197° C under 0.001 mm Hg (mixture of positional isomers).

EXAMPLE 6

While stirring a solution of 15.6 g of the compound of

TABLE I

| N° | —U$_1$ | —U$_2$ | —Y | Melting point in ° C |
|---|---|---|---|---|
| 59 | —C(CH$_3$)$_3$ | —H | —C$_2$H$_5$ | 96 – 97 |
| 60 | —C(CH$_3$)$_3$ | —H | —(CH$_2$)$_{11}$—CH$_3$ | 43 – 45 (b.p.230 – 235° C under 0.001 mm Hg) |
| 61 | —C(CH$_3$)$_3$ | —H | —CH$_2$—OC—O—CH$_3$ | 93 |
| 62 | —CH$_3$ | —H | —(CH$_2$)$_{11}$—CH$_3$ | 80 – 81 |
| 63 | —H | —CH$_3$ | —(CH$_2$)$_{11}$—CH$_3$ | 81 – 82 |
| 64 | —C(CH$_3$)$_3$ | —H | —CH$_2$—CH$_2$—S—CH$_2$—C(O)—HN—CH$_2$—[3,5-di-tert-butyl-4-hydroxyphenyl] | 193 – 196 |
| 65 | —CH$_3$ | —H | —CH$_2$—CH$_2$—S—CH$_2$—C(O)—HN—CH$_2$—[3-tert-butyl-5-methyl-4-hydroxyphenyl] | 162 – 163 |
| 66 | —H | —CH$_3$ | —C$_2$H$_5$ | 123 – 125 |
| 67 | —C(CH$_3$)$_3$ | —H | —C$_8$H$_{17}$ | 49 – 51 |
| 68 | —C(CH$_3$)$_3$ | —H | tertiary —C$_8$H$_{17}$ | 76 – 78 |
| 69 | —C(CH$_3$)$_3$ | —H | —C$_{18}$H$_{37}$ | 68 – 68.5 |
| 70 | —C(CH$_3$)$_3$ | —H | tertiary —C$_{12}$H$_{25}$ | thick oil |
| 71 | —C(CH$_3$)$_3$ | —H | —CH$_2$—COOC$_2$H$_5$ | 72 – 73 |

In a similar manner to that used for the manufacture of the compounds in Table I the compounds of the following formulae are obtained:

the formula (14) in 150 ml of absolute ethanol under nitrogen, 5.47 g of polythioformal H-(S-CH$_2$)$_t$SH [t = 4 on an average] and immediately afterwards 50 ml of N-absolute ethanolic sodium ethylate solution are stirred in. When the exothermic reaction has subsided, the batch is stirred on for 2 hours and the precipitated sodium chloride (2.85 g = 97.6% of theory) is suctioned off, and the filtrate is completely evaporated in vacuo.

The residue is subjected to fractional recrystallization from ½ liter of carbon tetrachloride, to yield various fractions of the compounds of the formula

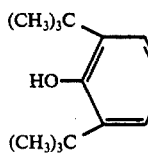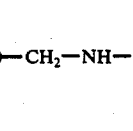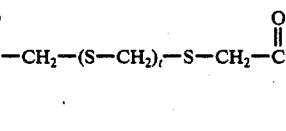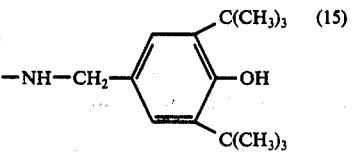

in which t has different mean values (from 2 to 5) which further contain 1 to 2 mols of carbon tetrachloride of crystallization which is given off quantitatively only after heating for 2 to 3 hours at 120° to 140° C under a high vacuum of 0.001 mm Hg.

From the first crystalline fraction there is thus obtained a product of the formula (15) in which t has an average value of 5 and which melts within the range from 145° to 151° C.

Most of the following crystalline fractions are less uniform and their mean t-values are lower.

EXAMPLE 7

A solution of 2.81 g of pentaerythritol-tetrathioglycollate in 40 ml of dimethylformamide is mixed with 8.1 g of the compound of the formula (14) and within 2 hours 2.6 ml of 10N-sodium hydroxide solution are stirred in dropwise under nitrogen. The batch is stirred in a stoppered flask for another 20 hours and then vigorously stirred into 800 ml of water. The precipitate is suctioned off and thoroughly washed with water, to yield 8.1 g (= 81% of theory) of the compound of the formula in 50 ml of normal absolute ethanolic or methanolic sodium hydroxide solution is boiled under a slight reflux under nitrogen for 2 hours or kept for 20 hours at room temperature. After this time the hydrolysis is substantially completed as can be shown by back-titrating against phenolphthalein. The solvent is then completely distilled off under a water-jet vacuum at 35° C, to furnish a glass-hard, friable residue (after drying in a desiccator) weighing about 19.5 g (100% of theory), being the compound of the formula

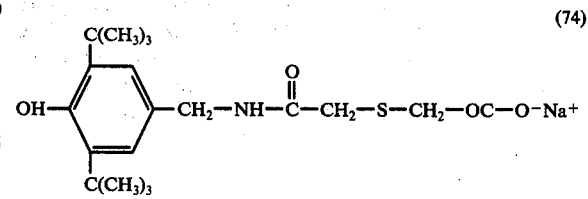

which decomposes at 201° – 205° C. This salt is soluble in water, ethanol, benzene and warm carbon tetrachloride.

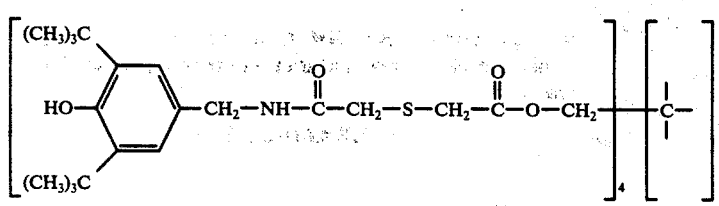

The product is best purified by chromatography on silica gel with an ascending series of eluants (benzene-chloroform). This furnishes the substance as a chloroform adduct from which chloroform can be quantitatively eliminated only by heating for 1 hour at 220° C under 0.001 mm Hg. Its melting range is from 101° to 109° C.

EXAMPLE 8

A solution of 19.25 g of the ester of the formula

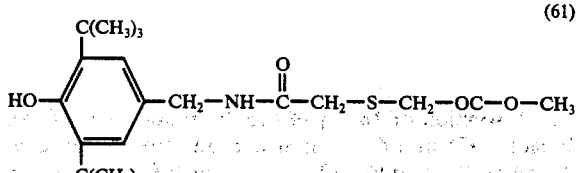

EXAMPLE 9

A solution of 19.25 g of the ester of the formula (61) in 50 ml of normal, absolute ethanolic sodium hydroxide solution are hydrolyzed as described in Example 8. The resulting solution of the sodium salt of the formula (74) is cooled to room temperature and mixed with a solution of 4.44 g of chromic chloride (CrCl$_3$.6 H$_2$O) in 45 ml of absolute ethanol, whereupon sodium chloride immediately begins to settle out. The batch is boiled under a slighht reflux for ½ hour and the precipitated sodium chloride (2.87 g = 98.4% of theory) is suctioned off. The filtrate is completely evaporated under vacuum. The blue-grey powdery residue is completely freed from impurities by being dissolved in 300 ml of xylene and agitated with 2 × 200 ml of water. Then 200 ml of xylene are distilled off under atmospheric pressure and the remainder under vacuum. The green, solid residue is dried for 3 hours at 50° C under a high vacuum and yields about 18.6 g (= 97% of theory) of the chromium salt of the formula

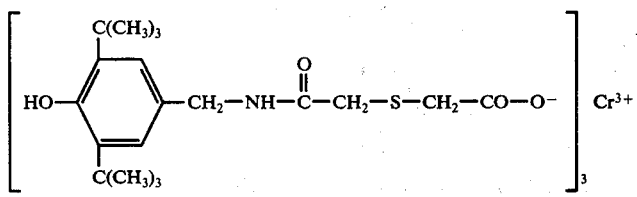

(75)

which turns at about 105° C into a glassy, soft product.

EXAMPLE 10

A solution of 7 g of the sodium salt of the formula (74) in 100 ml of water is mixed with a solution of 2 g of nickel chloride (NiCl$_2$.6 H$_2$O) in 50 ml of water, whereupon immediately a light-green, thick, unfilterable substance forms. The batch is thoroughly stirred with 300 ml of benzene until precipitated salt has dissolved completely in benzene. The benzolic phase is once more agitated with water and the bulk of benzene is distilled off under atmospheric pressure and the remainder under vacuum, to yield as a green, solid residue about 6.1 g (= 85.5% of theory) of the nickel salt of the formula

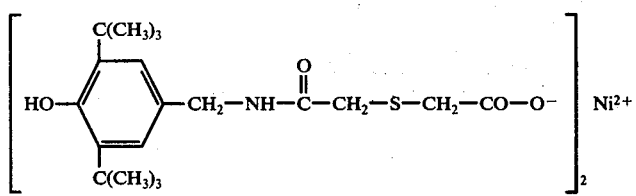

The salt is soluble in benzene and turns into a soft, glassy substance at about 180° C; it probably still contains water of crystallization. After having been dried for 3 hours over phosphorus pentoxide at 120° C under 0.001 mm Hg it dissolves only incompletely in benzene.

In an identical manner as the salts of the formulae (75) and (76) it is possible to manufacture the salts of the formula

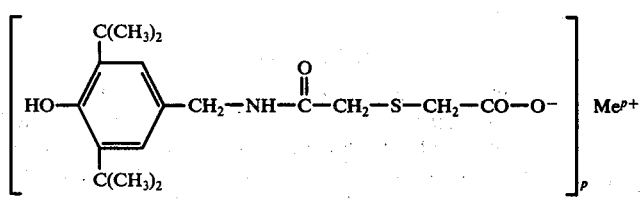

from suitable inorganic salts and the sodium salt of the formula (74).

TABLE II

| No | Me-salt | p | Softening temperature in ° C |
|----|---------|---|------------------------------|
| 78 | BaCl$_2$ . 6H$_2$O | 2 | 215 |
| 79 | CdCl$_2$ . H$_2$O | 2 | 125 |
| 80 | ZnCl$_2$ | 2 | 123 |
| 81 | SnCl$_2$ . 2H$_2$O | 2 | 67 |
| 82 | Pb(-acetate)$_2$2H$_2$O | 2 | 115 |
| 83 | CuSO$_4$ . 5H$_2$O | 2 | 199 |
| 84 | UO$_2$(-acetate)$_2$2H$_2$O (Me = UO$_2$) | 2 | 140 |
| 85 | CeCl$_2$ . 6H$_2$O | 3 | 125 – 130 |
| 86 | MnCl$_2$ . 4H$_2$O | 2 | 125 – 133 |

EXAMPLE 11

14 Grams of the compound of the formula (14) and 3.43 g of thiourea are dissolved at 50° C in 200 ml of absolute ethanol and kept for 3 hours at 50° C, then completely evaporated under a water-jet vacuum at room temperature. The viscid, clear residue begins to crystallize when allowed to stand for 1 day. Complete crystallization is achieved by trituration; yield: about 16.9 g (= 98% of theory) of the compound of the formula

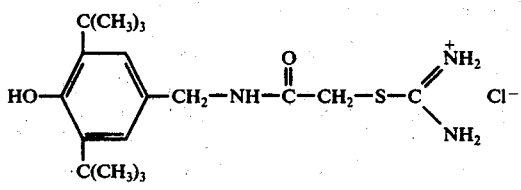

(87)

which decomposes at 104° C after reprecipitation from a mixture of ethanol and diethyl ether and is soluble in water.

EXAMPLE 12

(77)

a. A solution of 16.9 g of the thiuronium salt of the formula (87) in 100 ml of water free from oxygen is stirred at 50° C into 120 ml of oxygen-free N-sodium hydroxide solution. The insoluble phase is suctioned off and the filtrate rendered slightly acidic with 100% acetic acid, the precipitate is suctioned off and thoroughly washed with oxygen-free water, to yield about 6 g (= 44% of theory) of the mercapto compound of the formula

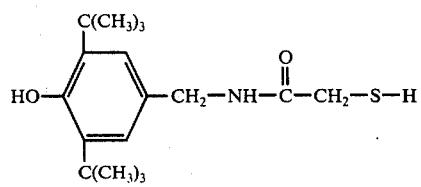 (18)

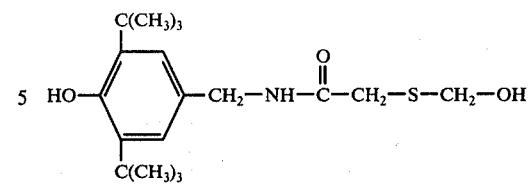 (19)

which melts at 146° – 147° C after recrystallization from 70% aqueous methanol.

b. A solution of 390 g of Na₂S (containing 40% of water of crystallization) in 3.6 litres of methanol is filtered to remove a small insoluble residue. H₂S gas is introduced to saturation and then a solution of 187 g of the compound (14) in 1.4 litres of methanol is added. The batch is stirred on for 4 hours while passing a weak current of hydrogen sulphide.

The solvent is then completely expelled under vacuum and the crystalline residue is taken up in 2.5 litres of oxygen-free water. If necessary, an insoluble residue is filtered off. While stirring well, 90 ml of 100% acetic acid are added, whereupon the product settles out first in smeary form but afterwards it crystallizes right as an oily residue which crystallizes right through after a few days. It melts at 104 to 106° C after recrystallization from benzene.

The bands of the bridged aliphatic hydroxyl group appear in the infrared spectrum at 3.02 and 9.17 μ.

EXAMPLE 14

A mixture of 10 g of the compound (18), 1.8 g of benzaldehyde and 0.3 g of p-toluenesulphonic acid in 150 ml of benzene is boiled for 7 hours in an apparatus equipped with a water separator, then cooled, agitated with 100 ml of N-sodium hydroxide solution and then thoroughly with water and dried over sodium sulphate. After having removed the solvent under vacuum a residue of 10.9 g (= 95% of theory) of the compound of the formula

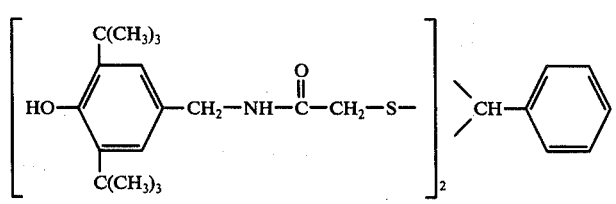 (21)

through quite rapidly.

For purification the reaction product is dissolved in 2 litres of oxygen-free N-sodium hydroxide solution; the insoluble phase is suctioned off and the filtrate is neutralized with 100% acetic acid. The precipitate is filtered off and thoroughly washed with water, to yield 132 g (= 71% of theory) of the compound of the formula (18).

EXAMPLE 13

A mixture of 7.8 g of the compound (18), 0.75 g of paraformaldehyde and 0.1 g of p-toluenesulphonic acid in 50 ml of benzene is refluxed for 30 minutes, then cooled, thoroughly agitated with 50 ml of N-sodium hydroxide solution and then several times with water and the benzolic phase is treated with sodium sulphate and active carbon. Removal of benzene under vacuum furnishes the product of the formula is obtained. During the recrystallization from carbon tetrachloride the solvent is incorporated and given off quantitatively only after heating for 30 minutes at 150° C under 0.001 mm Hg. Melting point: 108° – 110° C.

In an analogous manner compound (18) with n-heptaldehyde, lauraldehyde, stearaldehyde, with furfurol and with cyclohexanone respectively furnishes the compounds of the formulae

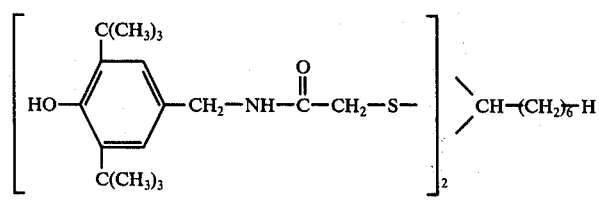 (22)

melting at 82° to 84° C

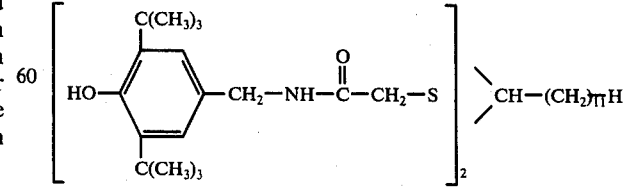 (22a)

melting at 84° to 89° C.

(22b)

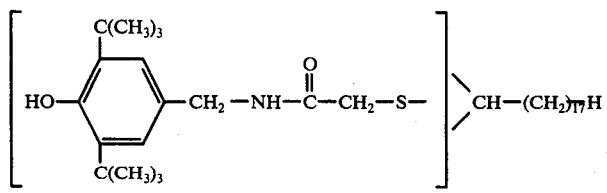

melting at 93° to 95° C.

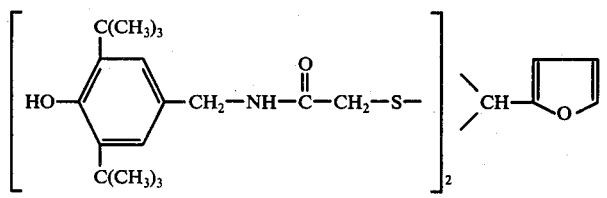

melting at 95° to 105° C.

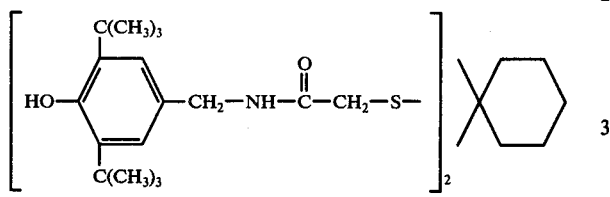

melting at 107° to 110° C.

EXAMPLE 15

15.5 Grams of the compound (18) are dissolved under nitrogen in 50 ml of N-absolute methanolic sodium ethylate solution, and 3.12 g of trans-1,4-dichlorobutene-(2) are added. When the strongly exothermic reaction has subsided, the batch is stirred for another 12 hours in a stoppered flask and the precipitated sodium chloride (2.4 g = 82% of theory) is suctioned off. The filtrate is completely evaporated and the residue treated with 50 ml of N-sodium hydroxide solution, washed free of alkali, and then dried, to yield 15.6 g (= 93% of theory) of the compound of the formula

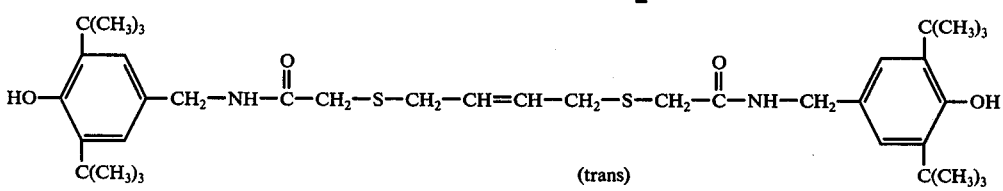

which after recrystallization from carbon tetrachloride contains 2 mols of carbon tetrachloride of crystallization. It melts at 101° – 103° C. It loses its carbon tetrachloride only after having been heated for 1 hour at 150° C under 0.001 mm Hg. The compound free from carbon tetrachloride melts at 91° – 101° C.

In an analogous manner compound (18) with 2,3-dichloropropene-(1), with methylenechloride or -bromide, with 1,4-dibromobutane and with 1,8-dibromooctane respectively furnishes the compounds of the formula (30) melting at 88° to 89° C, (31) melting at 150° to 151° C, (32) melting at 143° to 147° C, (33) melting at 70° to 78° C.,

EXAMPLE 16

12.4 Grams of the compound (18) are dissolved under nitrogen in 40 ml of N-absolute ethanolic Na-ethylate solution. The solvent is completely expelled at a bath temperature of 40° C under a water-jet vacuum and drying is performed for 6 hours under identical conditions. The residuue is the sodium salt of the compound of the formula (18) in form of a friable, hard substance.

The product is dissolved under nitrogen in 40 ml of dimethylformamide and 3.4 g of bromoform are added. The whole is kept overnight in a stoppered flask and then boiled for 3 hours at a slight reflux under nitrogen, then cooled and stirred into 400 ml of water with the aid of a high-speed stirrer. The precipitate is suctioned off and thoroughly washed with water, to yield 12.5 g (= 100% of theory) of the compound of the formula

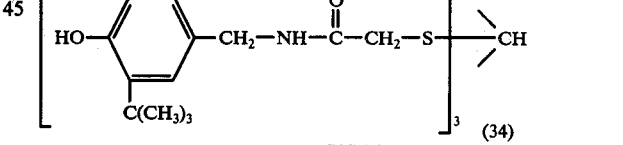

During recrystallization from carbon tetrachloride the solvent is incorporated and given off quantitatively only after heating for 1 hour at 75° C under 0.001 mm Hg. The substance softens in glassy form at 113° – 115° C.

The above produuct is also accessible by the use of chloroform instead of bromoform and also in an alcoholic solution.

In an analogous manner compound (18) with pentaerythritol-tetrabromide and with hexachloroethane respectively furnishes the compounds of the formula (36) melting at 130° – 134° C and (37) melting at 216° – 217° C.

EXAMPLE 17

A mixture of 15.6 g of the compound of the formula (14) and 12.4 g of powdered sodium thiosulphate.5H$_2$O in 200 ml of 80% aqueous methanol is stirred and refluxed for 1 hour, during which everything dissolves rapidly. The solvent is then completely expelled under vacuum and the solid residue is dried, dissolved in 200 ml of benzene and benzene is distilled off (about 50 ml) until water no longer appears in the distillate. The batch is cooled and the undissolved NaCl is filtered off (2.6 g = 89% of theory). The filtrate is completely evaporated and the residue dried for 1 hour at 120° C under vacuum, to yield 18.1 g (= 91% of theory) of the compound of the formula

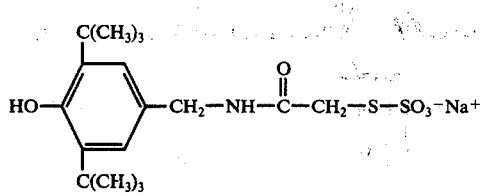

(88)

melting at 172° –178° C, which is soluble in benzene.

EXAMPLE 18

A solution of 15.6 g of the compound of the formula (14) in 200 ml of ethanol is mixed with 8.1 g of powdered sodium thiocyanate and the whole is heated to the boil with stirring, during which all dissolves. After a short time NaCl begins to settle out. The batch is refluxed for 3 hours, the precipitated NaCl is suctioned off and the filtrate is evaporated under vacuum. The crystalline residue is washed with water and recrystallized from a small quantity of methanol; the product melts at 143.5° to 145° C. A typical thiocyanate band appears in the infrared spectrum at 4.61μ.

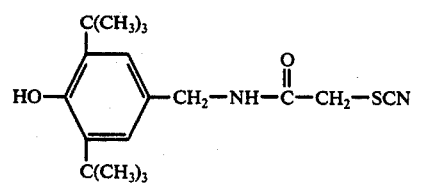

(89)

EXAMPLE 19

A mixture of 100 parts of unstabilized polypropylene and 0.02 part of one of the carboxylic acid amides of the formula (1) described in the preceding Examples is turned on a calender at 170° C into a sheet which is then rolled to and fro at 230° C under a pressure of 40 kg/cm$^2$ to form a panel 1 mm thick.

Tests performed with the resulting polypropylene panels by the methods A and B described below revealed the numerical values of Tables III and IV.

TEST METHOD A

The panel obtained as described is cut up into narrow strips which are allowed to age in an oven at 140° C until the naked eye can detect distinct fissures.

TABLE III

| Compound of formula added | Hours until fissures appear | Compound of formula added | Hours until fissures appear |
|---|---|---|---|
| (52) | 200 | (65) | 150 |
| (55) k = 5 | 200 | (79) | 110 |
| (56) | 150 | (80) | 100 |
| (60) | 550 | (81) | 100 |
| (62) | 150 | (18) | 150 |
| (64) | 250 | nil | 5 |

TEST METHOD B

The panel is shredded. 5 Grams of these chips are heated at 160° C in a reactor tube connected with an absolute pressure gauge, in an atmosphere of pure oxygen under a pressure of 700 mg Hg. By measuring the drop in pressure the induction time taken to reach the steep rise in the oxygen consumption can be determined. The resulting oxidation products are absorbed with the aid of a Linde molecular sieve 5A and of potassium hydroxide so that in each case the pressure measured corresponds to the residue of pure oxygen. Since many compounds develop their full antioxidative effect only at a lower temperature, the test is also performed at 100° C.

TABLE IV

| Added compound of the formula | Induction time in minutes at 160° C | at 100° C |
|---|---|---|
| (51) | 15 | 14 500 |
| (52) | 540 | 60 000 |
| (57) | 28 | 7 200 |
| (59) | 12 | 50 000 |
| (60) | 50 | 30 000 |
| (61) | 33 | 9 000 |
| nil | 2 | 50 |

EXAMPLE 20

The antioxidative effect of the compounds of the formula (1) can also be demonstrated in the test in which PVC panels are exposed to light. After PVC panels finished in this manner have been exposed to the fadeometer or the xeno test a distinct inhibition of yellowing is observed.

For these tests a mixture of suspension-PVC and commercial thermostabilizers and lubricants is formulated from
- 100 parts of suspension-PVC
- 2 parts of a tin stabilizer containing sulphur
- 2 parts of a lubricant based on esters of higher fatty acids
- 0.5 parts of a compound of the formula (1).

This mixture is turned into a sheet on a calender at 170° C which is then treated on a press at 180° C under a pressure of 40 kg/cm$^2$ to form a panel 1 mm thick. Panel sections manufactured in this manner are then exposed for 2000 hours in a xeno tester 150 or for 500 hours in a fadeometer (carbon ac).

Whereas the panels that do not contain an inhibitor of the formula (1) turn distinctly brownish after 800 hours in the xeno test or after 300 hours in the fadeometer, panels incorporating a compound of the formula (51) comprising an H$_3$C-(CH$_2$)$_{11}$ residue instead of the propyl residue 55, 60, 78, 81 or 85 show not the least sign of a change after the times indicated.

What we claim is:

1. A carboxylic acid amide of the formula

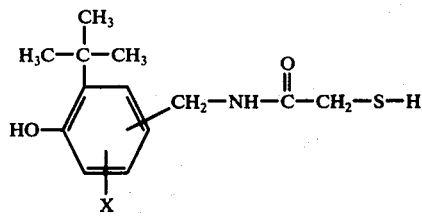

in which X is methyl or tertiary butyl.

2. A carboxylic acid amide according to claim 1 of the formula

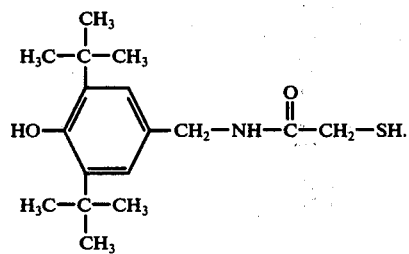

3. A carboxylic acid amide of the formula

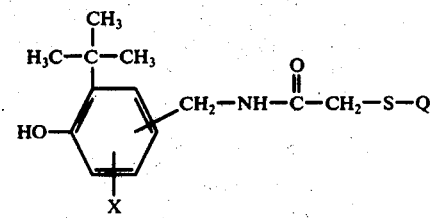

in which X is methyl or tertiary butyl and Q is alkyl containing 1 to 20 carbon atoms.

4. A carboxylic acid amide according to claim 3, wherein X is tertiary butyl and is located in ortho-position to the hydroxyl and the amido-methylene residue is located in paraposition to the hydroxyl.

5. A carboxylic acid amide according to claim 4 of the formula

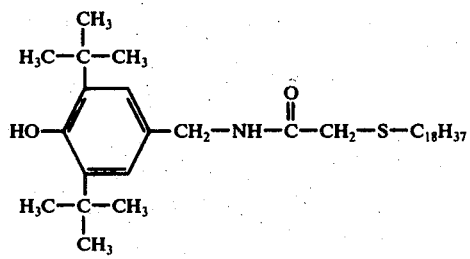

6. A carboxylic acid amide according to claim 4 of the formula

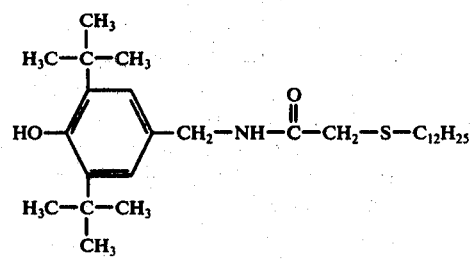

* * * * *